United States Patent
Gobet et al.

(10) Patent No.: US 7,192,411 B2
(45) Date of Patent: Mar. 20, 2007

(54) COMPRESSIVE ORTHOSIS FOR THE LOWER LIMB IN THE FORM OF A KNITTED ARTICLE OF THE STOCKING, SOCK, OR TIGHTS TYPE

(75) Inventors: Arnaud Gobet, Paris (FR); Francois Cros, Ivry sur Seine (FR)

(73) Assignee: Innothera Topic International, Arcueil (FR)

(*) Notice: Subject to any disclaimer, the term of this patent is extended or adjusted under 35 U.S.C. 154(b) by 83 days.

(21) Appl. No.: 11/158,330

(22) Filed: Jun. 22, 2005

(65) Prior Publication Data

US 2006/0247566 A1    Nov. 2, 2006

(30) Foreign Application Priority Data

May 2, 2005    (FR) .................................. 05 04436

(51) Int. Cl.
  *A61F 13/00* (2006.01)
  *D04B 9/46* (2006.01)
(52) U.S. Cl. ............................ 602/63; 602/62; 66/183; 2/239
(58) Field of Classification Search ............ 602/60–63, 602/75; 66/178 A, 178 R, 183, 184; 128/882, 128/883; 2/239–241, 54, 409
See application file for complete search history.

(56) References Cited

U.S. PATENT DOCUMENTS

| 3,856,008 | A |   | 12/1974 | Fowler et al. |
| 4,527,402 | A |   | 7/1985 | Swallow et al. |
| 5,412,957 | A | * | 5/1995 | Bradberry et al. ........ 66/178 A |
| 5,497,513 | A | * | 3/1996 | Arabeyre et al. ............... 2/240 |
| 6,216,495 | B1 | * | 4/2001 | Couzan et al. ................. 66/183 |
| 6,430,970 | B1 | * | 8/2002 | Gardon-Mollard et al. ......................... 66/178 A |
| 6,613,007 | B1 | * | 9/2003 | Reid, Jr. ...................... 602/75 |

FOREIGN PATENT DOCUMENTS

EP    0 705 543 A1    4/1996

* cited by examiner

*Primary Examiner*—Kim M. Lewis
(74) *Attorney, Agent, or Firm*—Jacobson Holman PLLC

(57) ABSTRACT

The orthosis comprises a leg portion and a foot portion. The leg portion which extends upwards from the ankle serves to apply therapeutic compression to the leg once the orthosis has been put on. The foot portion which extends from the malleolar region to the toes and covers the instep is a shaped portion that envelops the foot elastically. The dimensioning and the mesh structure of the foot portion are such that $0 < P_x < P_m < P_b$ once the orthosis has been put on, $P_x$ being the pressure applied to the instep region, $P_m$ being the pressure applied to the malleolar region, and $P_b$ being the therapeutic compression applied to the ankle region. Preferably, $P_x = 5$ mmHg±25% and $P_m = 0.5(P_b + P_x) \pm 25\%$.

6 Claims, 1 Drawing Sheet

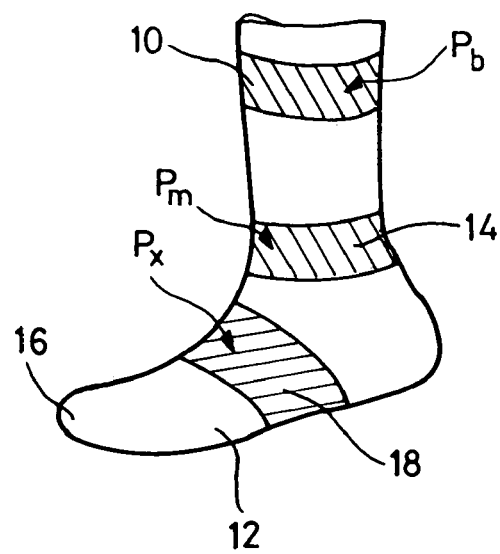
FIG_1
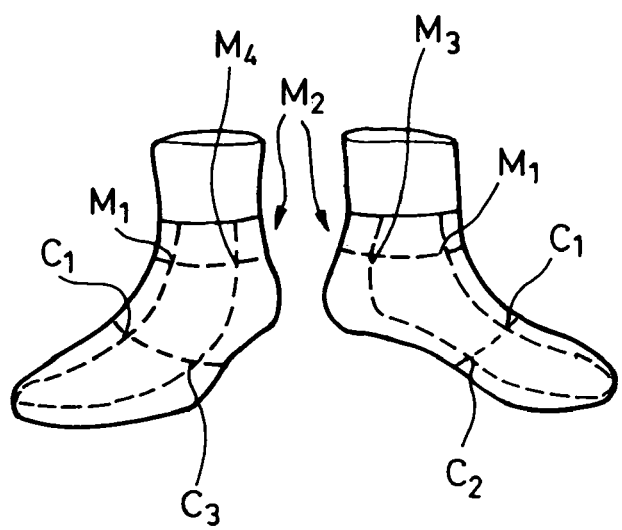
FIG_2
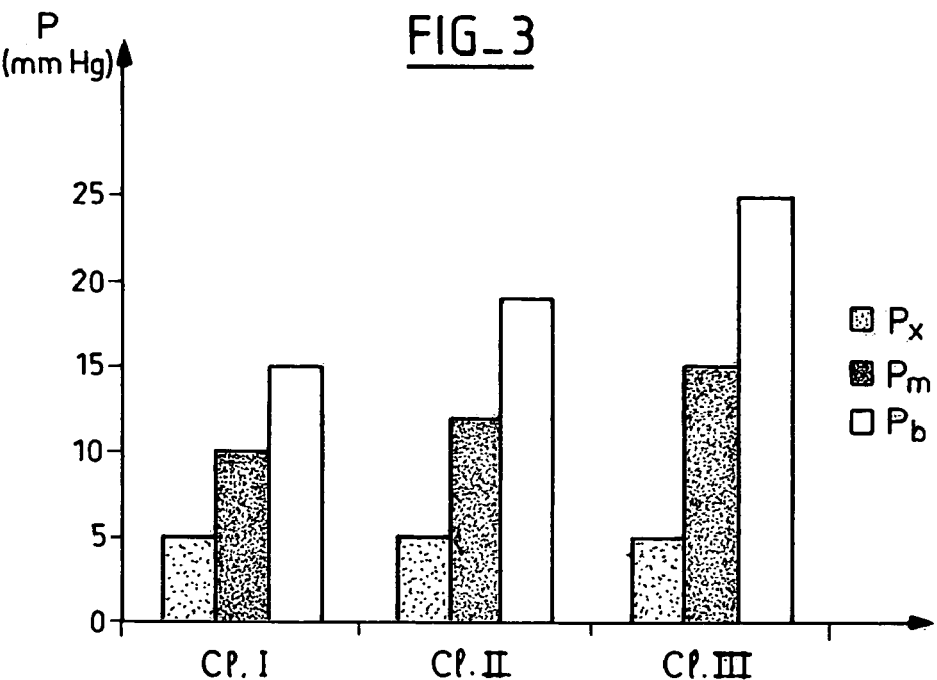
FIG_3

COMPRESSIVE ORTHOSIS FOR THE LOWER LIMB IN THE FORM OF A KNITTED ARTICLE OF THE STOCKING, SOCK, OR TIGHTS TYPE

FIELD OF THE INVENTION

The invention relates to orthoses generally known as "elastic stockings" or "elastic tights".

Although the term "stocking" is used below, the invention is not limited to one particular type of article, and it applies equally well to all forms of compressive orthoses for one or both lower limbs, whether in the form of tights, single-leg tights, stockings, or socks.

The invention relates more specifically to "elastic stockings" that are medical stockings producing a therapeutic effect by compressing/restraining the lower limbs, in opposition to "support stockings" (or "anti-tiredness stockings") and to "fashion stockings" which are not medical stockings having a therapeutic purpose.

BACKGROUND OF THE INVENTION

Medical elastic stockings are stockings which exert pressure as measured at the ankle lying in the range 10 millimeters of mercury (mmHg) to more than 36 mmHg (equivalent to 13 hecto pascals (hPa) to 48 hPa, but the present description nevertheless uses mmHg as the unit of pressure measurement, given that it is universally used in the field of phlebology and medical compression). According to the French standard, such stockings are subdivided into four compression classes, namely class I (10 mmHg to 15 mmHg at the ankle); class II (15 mmHg to 20 mmHg); class III (20 mmHg to 36 mmHg); and class IV (>36 mmHg).

In order to enable the lower limbs to be compressed strongly, such elastic stockings are made of an elastic material, typically a knit of very tight texture and also incorporating an elastic weft yarn (generally a covered elastane). They are dimensioned as a function of the patient's leg, so as to obtain, by elasticity, the looked-for pressure profile and degree of compression.

The starting point of the invention is the observation that numerous users of such elastic stockings complain of discomfit in the instep, and of significant cooling of the foot after wearing the stocking for a few hours. This phenomenon is due to the very tight texture of the elastic stocking, which is needed in order to produce a medical effect on the leg, but which leads to residual compression on the foot, in particular in the malleolar and instep regions, where said residual compression produces excess pressure leading to the above-mentioned drawbacks. These drawbacks do not appear with support stockings and fashion stockings since they exert much less pressure.

This phenomenon is particularly marked with elastic stockings that deliver a degressive pressure profile so that they exert their highest pressure at the ankle, i.e. in the vicinity of the foot joint, i.e. where medically speaking there is no need to exert much pressure (the term "foot" is used to mean the entire region of the lower limb going from the malleolar region—the bony crests of the tibia and the fibula—to the ends of the toes, with the "instep" being defined as the front top portion situated over the arch of the foot).

Applying compression to the foot presents no advantage that has been demonstrated, which is hardly surprising, insofar as:

- the anatomy of the arch of the foot lends itself poorly to compression, and any veins that might need compressing (in the sole) are under the arch. As a consequence of Laplace's equation, compression is very likely firstly to be vulnerable at the instep and the medial and external sides of the soles (1st and 5th radius) before possibly becoming effective at least to a small extent on the venous network of the sole ("Lejars' sole"). To be effective, it would be necessary to use an orthosis molded to have the shape of the arch of the foot (or to expect effectiveness only with subjects having grade 3 flat feet);
- in the prone position, the natural position of the foot is favorable to venous drainage of the front of the foot, whereas while standing the flattening of the sole doubtless has an effect in terms of compression that is better than anything that could be achieved by a highly compressive elastic stocking on the foot. The only vulnerable position is the sitting position associated with total inactivity of the foot and of the ankle.

In addition, there exist minor limits, or clear reserves, on applying compression to the foot:

- with some subjects, the arterial vascularization of the front of the foot is vulnerable specifically as a result of anatomy. Normally, this vascularization benefits from anastomosis between the network of the dorsal artery of the foot (anterior terminal branch of the tibial artery which runs along the instep and the back of the foot prior to going down between the metatarsal bones) and the medial plantar artery (posterior branch of the tibial artery which runs along the medial edge of the arch of the foot). Sometimes such anastomosis does not exist, and as a result arterial vascularization of the toes is made fragile. This is doubtless responsible for the feeling of cold feet in certain patients;
- in other patients, problems arise because of deformations of the metatarsus (hallux valgus, overlapping little toe, sag foot), still by the combination of "Laplace's equation+compression becoming excessive on a surface having a small radius of curvature";
- above all, in the event of severe arterial insufficiency (pressure index at the ankle <0.50), very distal arterial disease, vulnerable skin (diabetes with advanced microangiopathy, patients being treated over long term with corticotherapy, very aged subjects with cutaneous atrophy, . . . ), the iatrogenic risk of excess pressure on the instep and the back of the foot becomes highly perceptible. Under such circumstances, elasticated compression can be the result only of specialized advice.

In all, the only advantage in applying compression to the foot lies in:

- preventing edema and venous congestion in the instep due to too sudden a change in pressure going from the foot to the ankle (where the highest pressure is exerted); and
- to keep the stocking properly in place.

In addition, pressure at the foot is not controlled and consequently pressure at the instep can be even greater than the pressure exerted at the ankle.

OBJECTS AND SUMMARY OF THE INVENTION

One of the objects of the invention is to propose a medical elastic orthosis enabling the above drawbacks to be remedied by means of a new pressure profile designed specifically for the foot portion.

More precisely, the invention provides a medical elastic orthosis presenting a pressure profile in which the pressure delivered to the instep is reduced to a value close to that obtained with a non-medical fabric. In the malleolar region, pressure is delivered at a value lying between that delivered to the instep and the value prescribed for the ankle as a function of the selected class of compression. In this way, the orthosis presents a progressive pressure profile between the foot and the ankle, thereby making it possible to avoid a tourniquet effect at the ankle.

The orthosis of the invention is in the form of a knitted article of the stocking, sock, or tights type, comprising a leg portion and a foot portion. The leg portion which extends upwards from the ankle is a compressive tubular portion having a mesh structure and dimensioning that are selected so as to apply therapeutic compressive pressure on the leg once the orthosis has been put onto the limb. The foot portion which extends from the malleolar region to the toe region, covering the instep region, is a shaped portion having a mesh structure and dimensioning that are selected so as to envelop the foot elastically once the orthosis has been put on the limb.

In a manner characteristic of the invention, the mesh structure and the dimensioning of the foot portion are selected in such a manner as to satisfy the relationship $$0 < P_x < P_m < P_b$$

once the orthosis is in place on the limb, where $P_x$ is the pressure applied to the instep, $P_m$ is the pressure applied at malleolar level, and $P_b$ is the therapeutic compression applied to the ankle.

Preferably, the mesh structure and the dimensioning of the foot portion are selected so that $P_m < 0.8 P_b$, and/or so that the pressure $P_x$ at the instep is established at 5 mmHg±25%, and/or so that the pressure $P_m$ exerted on the retromalleolar zone becomes established at a value between those exerted on the instep and on the ankle, i.e. $P_m = 0.5(P_b + P_x) \pm 25\%$.

The pressure at the instep can be evaluated by averaging pressures taken on the top face, the medial face, and the external face of the instep region of the foot. The pressure in the malleolar region may be evaluated by averaging pressures taken from the front face, the anterior face, the posterior face, the medial face and the external face of the malleolar region.

BRIEF DESCRIPTION OF THE DRAWING

An embodiment of the invention is described below with reference to the accompanying drawing, in which the same references are used from one figure to another to designate items that are identical or functionally similar.

FIG. 1 is a diagrammatic view showing the various zones concerned by the pressure profile of the orthosis of the invention.

FIG. 2 shows the various measurement points that can be used for picking up and calculating pressure data.

FIG. 3 shows the pressures exerted respectively on the instep, on the malleolar region, and on the ankle, for orthoses of the invention in classes I, II, and III.

MORE DETAILED DESCRIPTION

FIG. 1 shows the various regions of the bottom portion of the orthosis, which is an orthosis that is closed in its bottom portion, i.e. it completely envelops the foot, e.g. like a sock, a stocking, or tights.

These various regions comprise a leg portion 10 extending upwards from the ankle (and including the ankle region), a foot portion 12 extending from the malleolar region 14 (and including the malleolar region) as far as the toe region 16, and covering the intermediate region 18 of the instep.

The leg portion 10 is a compressive tubular portion, itself conventional and unmodified, having a mesh structure and dimensioning that are selected so as to apply therapeutic compression to the leg once the orthosis has been put on said limb.

The stitch used may be of the same type as those used in conventional elastic stockings, for example of the weft, plain, pinched or float micromesh, etc. type, all stitches that are themselves known to specialists in knitting techniques. Concerning the yarn selected for knitting the orthosis, it may be cotton-and-polyamide covered elastane, polyamide-without-cotton covered elastane, or indeed a mixture of elastane and elastodiene (synthetic rubber latex).

The selected stitch and yarn, and also the dimensioning of the various rows of stitches, are defined so as to apply predetermined pressures at different heights up the leg, for example at ankle height, at the beginning of the calf, at the calf, behind the knee, etc. up to the top of the thigh for a thigh-length stocking or tights. These various pressures are defined for each compressive class with reference to measuring templates such as the Hohenstein model: for a given height, the structure of the row of stitches ensures that elastic return forces are uniformly distributed around the circumference of the stocking, i.e. along a contour corresponding to a horizontal section of the limb. For a circular contour, as applies to Hohenstein models, the application of such elastic return forces to the perimeter of the corresponding circular outline leads, at any given point, and in application of Laplace's equation, to local pressure that is inversely proportional to the radius of curvature of the outline at said point.

Under present circumstances, it is considered essentially that the pressure exerted at a height known as the "point b" height in the Hohenstein model, i.e. at ankle level, is the prescribed pressure for the selected compressive class (I, II, III, or IV), and which also corresponds to the value of the (theoretically) highest pressure that is exerted on the limb. The foot portion is a shaped portion, i.e. it is designed to match the shape of the foot, and its mesh structure and dimensioning are selected so as to envelop the foot elastically once the orthosis has been put on the limb, so as to ensure that the leg portion is held properly without wrinkles forming and without the orthosis material moving relative to the leg while walking.

Given the morphology of the foot and the presence of bones in the malleolar region 14 and in the instep region 18, compression is not uniform around the entire outline. The pressure $P_m$ applied to the malleolar region and the pressure $P_x$ applied to the instep region are then defined on the basis of averaging local pressure measurements taken at a plurality of points.

FIG. 2 shows an example of measurement points for evaluating these pressure values.

For the malleolar region, the pressure can be measured at four points distributed as follows: $M_1$ on the anterior face; $M_2$ on the posterior face; $M_3$ on the medial face; and $M_4$ on the external face, immediately below the ankle bone. For the instep region of the foot, these points may be distributed as follows: $C_1$ on the top of the foot; $C_2$ on the medial face; and $C_3$ on the external face. The pressure parameter $P_m$ is the mean of the four values $M_1$ to $M_4$ taken in this way; similarly the pressure $P_x$ is the mean of the three values $C_1$ to $C_3$ taken in this way.

These pressures may be measured using conventional sensors (Salzmann type or other sensors) that measure the pressure produced locally by the orthosis by delivering an electrical signal that can subsequently be converted and processed for various kinds of calculation and display.

The invention proposes a novel pressure profile to be exerted on the foot by the elastic orthosis (with the pressure profile for the leg portion remaining unchanged).

The orthosis is thus designed to deliver pressure at the instep equal to 5 mmHg, for example, i.e. a value close to that delivered by a non-medical fabric, and sufficient to enable the foot to be enveloped and the orthosis to be held in place without inconveniencing the subject.

In the malleolar region, the orthosis is modified to produce a pressure value $P_m$ at this location having an intermediate value, advantageously halfway between the $P_x=5$ mmHg exerted at the instep and the value $P_b$ required at point b (where this value depends on the selected compression class). Thus, by way of example, the orthosis is suitable for delivering pressure in the malleolar region as follows:

$P_m$=7.5 mmHg to 10 mmHg for a class I product (where $P_b$=10 mmHg to 15 mmHg);

$P_m$=10 mmHg to 12.5 mmHg for a class II product (where $P_b$=15 mmHg to 20 mmHg);

$P_m$=12.5 mmHg to 20.5 mmHg for a class III product (where $P_b$=20 mmHg to 36 mmHg); and $P_m$<36 mmHg for a class IV product (where $P_b$>36 mmHg).

This progressive arrangement, expressed by the following relationship:

$$0<P_x<P_m<P_b$$

serves to avoid a tourniquet effect at point b.

FIG. 3 thus shows examples of pressures $P_x$, $P_m$ and $P_b$ for orthoses of the invention in classes I, II, and III.

Above point b, the product remains in compliance with the requirements of regulations, and, regardless of its class, therefore needs no new certification compared with an existing product.

The low pressures applied to the feet are likely in particular to improve patient compliance with the application of elastic compression to treat venous disorders, and can thus contribute to the therapeutic effectiveness of the treatment in the long term.

What is claimed is:

1. A compressive orthosis for the lower limb, the orthosis being in the form of a knitted article of the stocking, sock, or tights type, and comprising:

a leg portion extending upwards from the ankle, said leg portion being a compressive tubular portion of mesh structure and dimensioning selected in such a manner as to apply therapeutic compression to the leg once the orthosis has been put on the limb; and a foot portion extending from the malleolar region to the toe region covering the instep region, said foot portion being a shaped portion of mesh structure and dimensioning that are selected so as to envelop the foot elastically once the orthosis has been put on the limb;

wherein the mesh structure and the dimensioning of the foot portion are selected in such a manner that once the orthosis has been put on the limb:

$$0<P_x<P_m<P_b$$

$P_x$ being the pressure applied by the orthosis level with the instep;

$P_m$ being the pressure <36 mm Hg applied by the orthosis level with the malleolar region; and $P_b$ being said therapeutic compression applied by the orthosis level with the ankle.

2. The orthosis of claim 1, in which the mesh structure and the dimensioning of the foot portion are selected in such a manner that $P_m<0.8P_b$.

3. The orthosis of claim 1, in which the mesh structure and the dimensioning of the foot portion are selected in such a manner that $P_x=5$ mmHg±25%.

4. The orthosis of claim 1, in which the mesh structure and the dimensioning of the foot portion are selected in such a manner that $P_m=0.5(P_b+P_x)5±25\%$.

5. The orthosis of claim 1, in which the pressure applied by the orthosis in the region of the instep is an average of pressure measurements taken from the top face, the medial face, and the external face of the instep region of the foot.

6. The orthosis of claim 1, in which the pressure applied by the orthosis in the malleolar region is an average of pressure measurements taken from the anterior face, the posterior face, the medial face, and the external face of the malleolar region.

* * * * *